United States Patent [19]
Yoon

[11] Patent Number: 6,159,224
[45] Date of Patent: Dec. 12, 2000

[54] MULTIPLE NEEDLE SUTURING INSTRUMENT AND METHOD

[76] Inventor: InBae Yoon, 2101 Highland Ridge Dr., Phoenix, Md. 21131

[21] Appl. No.: 09/300,011

[22] Filed: Apr. 28, 1999

Related U.S. Application Data

[63] Continuation-in-part of application No. 08/758,648, Nov. 27, 1996, Pat. No. 5,759,188.

[60] Provisional application No. 60/083,622, Apr. 30, 1998.

[51] Int. Cl.⁷ .................................................. A61B 17/04
[52] U.S. Cl. ........................ 606/147; 606/139; 606/144; 606/145
[58] Field of Search ................................. 606/139, 144, 606/145, 147, 148, 219, 222

[56] References Cited

U.S. PATENT DOCUMENTS

| | | | |
|---|---|---|---|
| 919,138 | 4/1909 | Drake . | |
| 1,037,864 | 9/1912 | Carlson . | |
| 1,449,087 | 5/1923 | Bugbee . | |
| 1,822,330 | 9/1931 | Ainslie . | |
| 2,213,830 | 9/1940 | Anastasi | 128/340 |
| 2,646,045 | 7/1953 | Priestley | 128/340 |
| 2,959,172 | 11/1960 | Held | 128/340 |
| 3,090,386 | 5/1963 | Curtis | 128/334 |
| 3,139,089 | 6/1964 | Schwerin | 128/340 |
| 3,349,772 | 10/1967 | Rygg | 128/340 |
| 3,470,875 | 10/1969 | Johnson | 128/334 |
| 3,842,840 | 10/1974 | Schweizer | 128/334 R |
| 3,946,740 | 3/1976 | Bassett | 128/334 R |
| 4,164,225 | 8/1979 | Johnson | 128/334 R |
| 4,440,171 | 4/1984 | Nomoto | 128/335.5 |
| 4,621,640 | 11/1986 | Mulhollan | 128/340 |
| 4,635,638 | 1/1987 | Weintraub | 128/340 |
| 4,935,027 | 6/1990 | Yoon | 606/146 |
| 5,037,433 | 8/1991 | Wilk | 606/139 |
| 5,100,421 | 3/1992 | Christoudias | 606/147 |
| 5,147,373 | 9/1992 | Ferzli | 606/144 |
| 5,181,919 | 1/1993 | Bergman | 606/144 |
| 5,234,443 | 8/1993 | Phan | 606/148 |
| 5,244,948 | 9/1993 | Mulhaupt | 524/99 |
| 5,261,917 | 11/1993 | Hasson | 606/139 |
| 5,281,238 | 1/1994 | Chin | 606/148 |
| 5,292,326 | 3/1994 | Green et al. | 606/143 |
| 5,336,230 | 8/1994 | Leichtling | 606/148 |
| 5,336,231 | 8/1994 | Adair | 606/148 |
| 5,356,424 | 10/1994 | Buzerak | 606/223 |
| 5,364,408 | 11/1994 | Gordon | 606/144 |
| 5,374,275 | 12/1994 | Bradley | 606/144 |
| 5,389,098 | 2/1995 | Tsuruta | 606/41 |
| 5,389,103 | 2/1995 | Melzer | 606/144 |
| 5,395,367 | 3/1995 | Wilk | 606/1 |
| 5,397,325 | 3/1995 | Della Badia | 606/144 |
| 5,454,823 | 10/1995 | Richardson | 606/148 |
| 5,470,338 | 11/1995 | Whitfield | 606/144 |
| 5,474,057 | 12/1995 | Makower | 600/214 |
| 5,477,794 | 12/1995 | Klundt | 112/169 |
| 5,478,344 | 12/1995 | Stone | 606/144 |
| 5,478,345 | 12/1995 | Stone | 606/144 |
| 5,480,406 | 1/1996 | Nolan | 606/139 |
| 5,496,334 | 3/1996 | Klundt | 606/145 |
| 5,520,703 | 5/1996 | Essig | 606/148 |
| 5,540,704 | 7/1996 | Gordon | 606/144 |
| 5,540,705 | 7/1996 | Meade | 606/145 |
| 5,545,148 | 8/1996 | Wurster | 604/223 |
| 5,562,640 | 10/1996 | McCabe | 604/280 |
| 5,562,685 | 10/1996 | Mollenauer | 606/144 |
| 5,562,686 | 10/1996 | Sauer | 606/144 |
| 5,562,703 | 10/1996 | Desai | 606/210 |
| 5,569,164 | 10/1996 | Lurz | 600/158 |
| 5,569,269 | 10/1996 | Hart | 606/144 |
| 5,569,270 | 10/1996 | Weng | 606/144 |
| 5,573,542 | 11/1996 | Stevens | 606/144 |
| 5,578,048 | 11/1996 | Pasqualucci | 606/192 |
| 5,591,181 | 1/1997 | Stone | 606/144 |
| 5,609,601 | 3/1997 | Kolesa | 606/170 |

*Primary Examiner*—Gary Jackson
*Attorney, Agent, or Firm*—Blank, Rome, Comisky & McCauley LLP

[57] ABSTRACT

A suturing instrument having needle holders for passing a needle through anatomical tissue. Needles are dispensed from an integral portion of the instrument and loaded into a needle holder prior to suturing. When a suturing procedure is completed, the needle is collected into an integral portion of the instrument.

34 Claims, 10 Drawing Sheets

MULTIPLE NEEDLE SUTURING INSTRUMENT AND METHOD

RELATED APPLICATION DATA

This application is a continuation-in part of applicant's application Ser. No. 08/758,648 filed on Nov. 27, 1996, now U.S. Pat. No. 5,759,188, the disclosure of which is incorporated herein by reference. Also, this application is related to applicant's copending application Ser. Nos. 08/847,252, 08/847,189, 08/847,253 and 08/847,254 and the copending application entitled Surgical Instrument with Movable Arcuately Offset End Effectors and Method of Using the Same, filed on Jul. 23, 1997, the disclosures of which are also incorporated herein by reference. This appln claims benefit of provisional appln 60/083,622 Apr. 30, 1998.

BACKGROUND OF THE INVENTION

1. Field of the Invention

The present invention pertains to suturing of bodily or anatomical tissue and, more particularly, to an instrument and method for suturing anatomical tissue during endoscopic and open surgical procedures in which multiple suturing procedures can be accomplished without withdrawing the instrument for reloading with needles.

2. Discussion of the Related Art

Suturing of bodily tissue, that is, the practice of using lengths of suture material to ligate or approximate tissue, is a time consuming part of most surgical procedures including both open surgery and endoscopic or closed surgery. "Open surgery" refers to surgery wherein the surgeon gains access to the surgical site by a relatively large incision and "endoscopic surgery" refers to any minimally invasive surgery wherein the surgeon gains access to the surgical site via one or more portals through which endoscopes are introduced to view the surgical site and through which instruments, such as forceps, cutters, needle holders, clip appliers, and the like, are introduced to the surgical site.

In the past, suturing has been accomplished with the use of a sharp suture needle carrying a length of suture material, the suture needle being caused to penetrate and pass through the tissue pulling the suture material through the tissue. Once the suture material has been pulled through the tissue, the surgeon ties a knot in the suture material, the knotting procedure allowing the surgeon to adjust the tension on the suture material to accommodate the particular tissue being sutured and to control approximation, occlusion, attachment or other conditions of the tissue.

The process of tissue penetration and knotting of the suture material can be time consuming and tedious work, particularly when performed in connection with microsurgery and endoscopic surgery, and can unduly prolong the duration of surgery and therefore the period in which the patient is under anesthesia. Nevertheless, endoscopic surgery is preferred over open surgery due to the greatly reduced trauma and wound healing time for the patient and due to cost savings associated with shorter hospital stays and performing surgery in non-hospital or out-patient surgery sites. Accordingly, there has been much effort to develop techniques for facilitating the suturing normally performed by use of a suture needle and a length of suture material. Alternative techniques proposed have included electrical coagulation, mechanical devices such as clips, clamps and staples, and lasers. However, no alternative technique has yet been well accepted by surgeons to produce the results obtained by suturing and tying. Thus, there is a great need for suturing techniques useful in endoscopic surgery, and open surgery, to permit surgeons to suture anatomical tissue using suture needles and lengths of suture material in a time efficient, consistent and precise manner.

The performance of an endoscopic procedure typically involves creation of one or a number of puncture sites through a wall of an anatomical cavity using a penetrating instrument including an obturator, such as a trocar, disposed within a portal sleeve. After the penetrating instrument has penetrated into the anatomical cavity, the obturator is withdrawn leaving the sleeve in place to form a portal in the cavity wall for the introduction of instruments such as endoscopes, scissors, forceps, needle holders and the like into the anatomical cavity. Suturing is typically performed with a needle holding instrument or holder having a pair of jaws adapted to hold the body of a suture needle. The jaws of the needle holding instrument are inserted through the portal sleeve and are positioned at the operative site by manipulation of a handle at the proximal end of the instrument outside the body.

With a suture needle held between the jaws of the needle holding instrument, the handle is manipulated to cause a tip of the needle to be pushed through the tissue being sutured. Once the tip of the suture needle has been pushed through the tissue, the jaws of the needle holding instrument must either be opened to release the suture needle so that the tip of the needle can be grasped and pulled through the tissue therewith, or a second needle holding instrument must be introduced at the operative site through another portal to grasp the tip of the suture needle after it has emerged from the tissue being sutured. The former technique requires further adjustment of the suture needle within the jaws of the needle holder before another stitch can be made; and, while use of a second needle holding instrument for pulling the needle through the anatomical tissue allows the first needle holding instrument to grasp the body of the suture needle in the manner required to make additional stitches, it is generally desirable to minimize the number of puncture sites created for performing a particular endoscopic procedure.

It is known to provide a suturing instrument having two needle holders such as is disclosed in U.S. Pat. No. 5,100,421 issued to Christoudias. This facilitates suturing. However, the instrument disclosed by Christoudias must be reloaded with a needle having suture material attached thereto after each suturing operation. Reloading can be accomplished by withdrawing the instrument and inserting a new needle in one of the needle holders or by introducing a new needle with another instrument. The former procedure requires a great deal of time and withdrawal of the instrument and the latter procedure requires another puncture to accommodate the needle loading instrument. Of course, both of these requirements are generally undesirable.

Needle loading cartridges have been used to position a needle properly in a needle holder and to facilitate handling of needles. However, known needle cartridges are relatively large instruments separate from the suturing instrument and are designed to be used while the needle holder is withdrawn from a cavity. Therefore, there is no satisfactory instrument for accomplishing multiple suturing procedures without withdrawing the instrument or creating an additional puncture. It is known to integrate cartridges or magazines into clip appliers, staplers, or the like. However, clips and staples are relatively small, simple in mechanical construction, and do not require the loading precision that is required in a suturing process. Therefore, prior art devices do not permit multiple needles to be housed integrally in a suturing instrument and loaded into a needle holder as needed. Also, prior art devices do not allow for recovering a needle after use. This requires that each used needle be removed with the suturing instrument, or another instrument, immediately after use because needles left in an anatomical cavity even for a short period of time can cause tissue damage.

SUMMARY OF THE INVENTION

Accordingly, it is a primary object of the present invention to overcome the above-mentioned disadvantages of the prior art and to improve suturing instruments and methods of suturing anatomical tissue.

It is another object of the present invention to permit a suturing instrument to be reloaded with needles and suture without the need for withdrawing the suturing instrument from the cavity or the need of introducing a separate needle loading instrument.

It is another object of the invention to protect needles from damage or from contamination by eliminating the need for handling of individual needles.

It is yet another object of the invention to permit multiple needles to be housed in a suturing instrument or other instrument and to be advanced in seriatim into the needle grasping portion of a needle holder of the instrument.

It is another object of the invention to retrieve multiple used needles into the suturing instrument.

It is a further object of the present invention to permit a suturing instrument as well as other medical instruments to be introduced through a single portal in an endoscopic procedure without the need of having to withdraw the suturing instrument from the portal.

It is a further object of the invention to suture, tie suture material, and cut suture material with a simple instrument.

Yet another object of the present invention is to minimize the number of puncture sites required for suturing anatomical tissue in an endoscopic procedure by inserting a pair of needle holders through a single puncture site with a suturing instrument having a handle operable to move the needle holders relative to one another in a cooperative manner to suture anatomical tissue.

Some of the advantages of the present invention over the prior art are that suturing of anatomical tissue can be accomplished in a time efficient, consistent and precise manner, that suturing can be accomplished using standard suture needles and filamentous suture materials without the need of having to insert additional instruments at the operative site, that single-handed suturing is made possible, that conventional handle structures can be used to provide users with a familiar feel and to decrease adaptation time, and that multiple suturing procedures can be easily accomplished.

The present invention is generally characterized in an instrument for suturing anatomical tissue with a suture needle including a barrel or outer tubular member, a needle driver mounted in the barrel for movement along a first arcuate path, and a needle catcher mounted in the barrel for movement along a second arcuate path. The needle driver and the needle catcher each include needle holding members selectively operable to grasp and release the suture needle so that, when the needle holding members of the driver are operated to grasp the suture needle, the driver can be rotated to drive the suture needle through anatomical tissue positioned between the driver and the catcher, and when the needle holding members of the catcher are operated to grasp the suture needle, the needle holding members of the driver can be operated to release the suture needle, thereby allowing the catcher to be rotated to pull the suture material through the anatomical tissue.

A needle dispensing cartridge, or magazine, is disposed in a channel defined in the distal end of the barrel and is operative to eject a plurality of needles, one at a time, and place the needles in the needle holding members of the needle driver or the needle catcher. Also, a needle collecting cartridge, or magazine, is disposed in a channel defined in a distal end of the barrel and is operative to collect needles from the needle catcher or the needle driver after the needles have been used for a suturing procedure. The needle collecting cartridge and the needle dispensing cartridge, i.e. the needle cartridges, are integral with the instrument. The term "integral" as used herein means that the cartridges or other needle storing elements, are attached to, or contained in, the instrument and do not require separate insertion into the cavity. The cartridges can be omitted and the needles can be housed directly in the suturing instrument.

Another aspect of the present invention is generally characterized in a method of suturing anatomical tissue using a length of suture material attached to a suture needle. The method includes the steps of ejecting a needle from a needle dispensing cartridge disposed in a barrel, grasping the suture needle with a first needle holder mounted in the barrel, positioning the anatomical tissue between a tip of the suture needle and a second needle holder mounted in the barrel, rotating the first needle holder in a first direction along an arcuate path to cause the tip of the needle to penetrate the anatomical tissue, receiving the tip of the suture needle in the second needle holder, grasping the suture needle with the second needle holder, releasing the suture needle from the first needle holder, rotating the second needle holder in the first direction along a second arcuate path to pull the needle and the suture material through the anatomical tissue, and retrieving the needle in a needle collecting cartridge disposed in the barrel.

Other objects and advantages of the present invention will become apparent from the following description of the preferred embodiments taken in conjunction with the accompanying drawings, wherein like parts in each of the several figures are identified by the same reference numerals.

DESCRIPTION OF THE PREFERRED EMBODIMENTS

The suturing instrument of the present invention can be utilized to suture any type of anatomical tissue in any type of anatomical cavity; and, accordingly, while the instrument is described hereinafter for use with a portal sleeve in endoscopic procedures, such as laparoscopy, the instrument can be used in open surgery and with catheters and other small and large diameter tubular or hollow, cylindrical members providing access to small cavities, such as veins and arteries, as well as large cavities, such as the abdomen or in conventional open surgical procedures.

Figure 1:
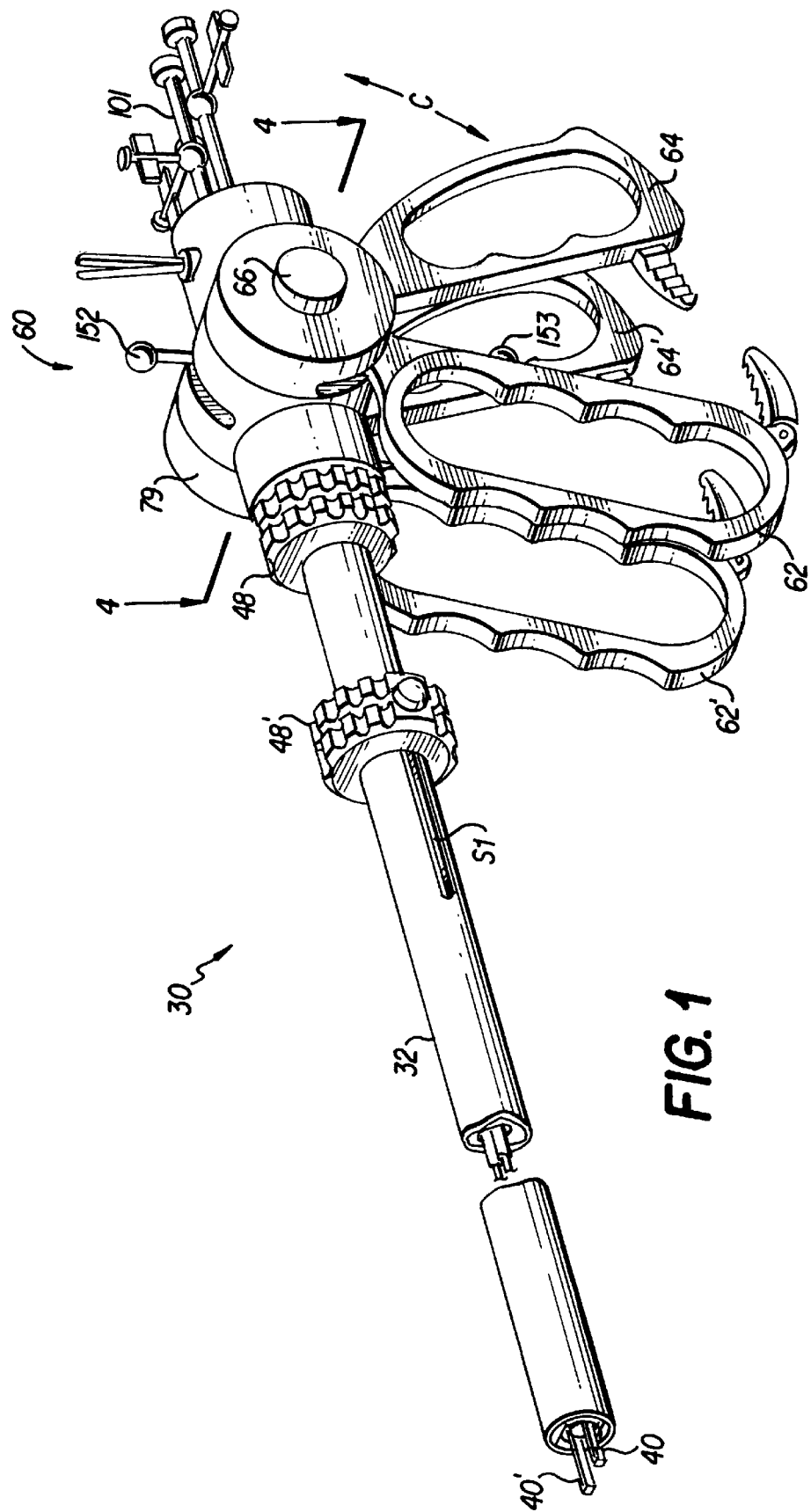
FIG. 1 is a perspective view of a preferred embodiment of the invention.

A suturing instrument according to a first preferred embodiment of the present invention is illustrated at 30 in FIG. 1 and includes cylindrical barrel, or outer shaft, 32 which has an elongated passage defined therein, needle driver 40, and needle catcher 40'. Needle driver 40 and needle catcher 40' are substantially contained within cylindrical barrel 32 as is described in detail below. The terms "needle driver" and "needle catcher" are used herein to describe, in terms of their function in the preferred embodiment, elements that may be structurally similar in the preferred embodiment. However, the function of these two elements herein is interchangeable. Also, these elements are sometimes referred to generically as "needle holders" herein. Also, similar elements having various end effectors, including but not limited to needle holding members, may be referred to as "drivers", "operators", "supports", or "assemblies" herein and refer to any structure associated with an end effector whether or not the structure imparts function to the end effector. As shown by arrows A and B in FIG. 1, needle driver 40 and needle catcher 40' can be moved, independently of one another, proximally and distally in barrel 32. This movement will be described in detail below.

Figure 2:
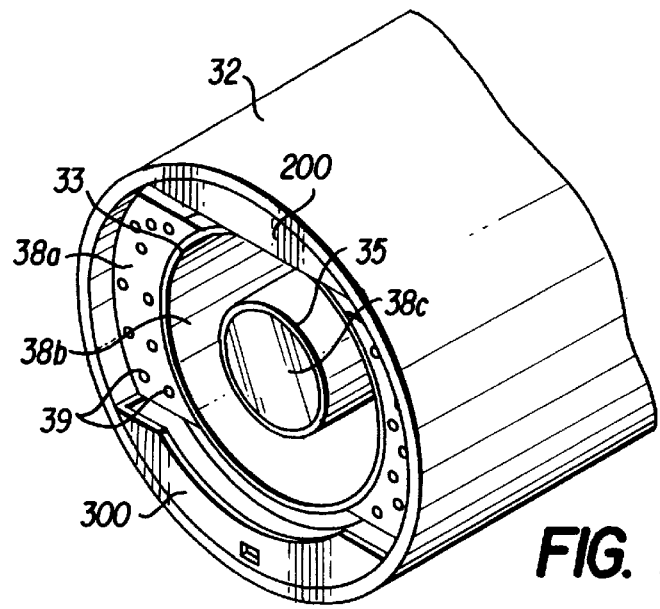
FIG. 2 illustrates the distal end of the barrel of the preferred embodiment.
Figure 5A:
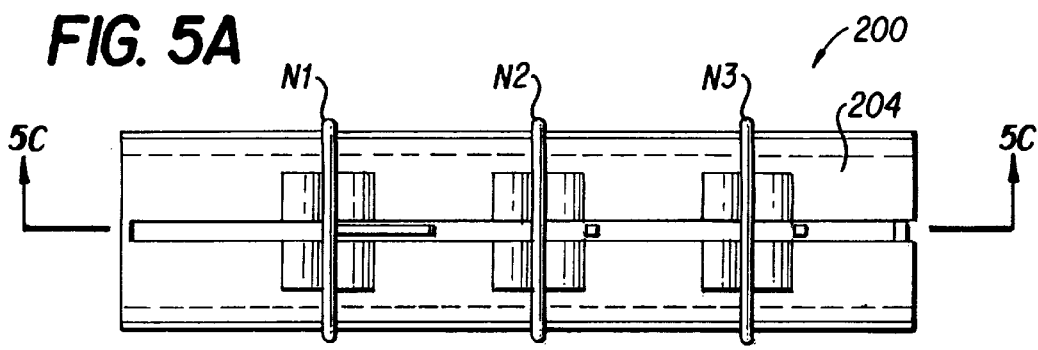
FIG. 5A illustrates is a top view of the needle dispensing cartridge of the preferred embodiment with the top portion of the housing removed.
Figure 5B:
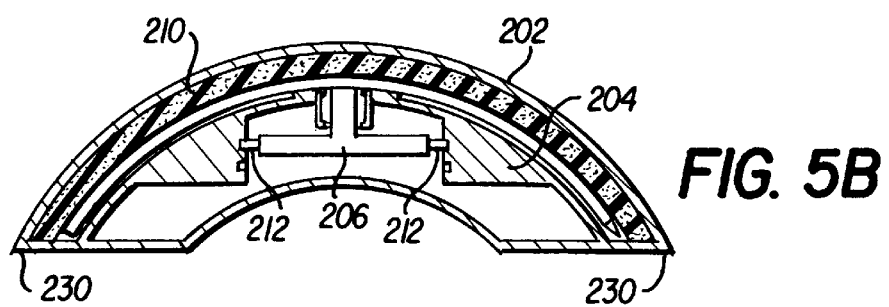
FIG. 5B illustrates the needle dispensing cartridge in cross-section taken along line 5B—5B of FIG. 5C.

As shown in FIG. 2 which illustrates a distal end of barrel 32 with needle driver 40 and needle catcher 40' removed for illustrative purposes, barrel 32 has annular channels 38a and 38b defined therein by tubular intermediate sleeve 33 and tubular inner sleeve 35. Central channel 38c is defined inside inner sleeve 35. Barrel 32 can have additional channels for receiving one or more additional instruments, or to be used for suction, aspiration, or the like, or barrel 32 can have fewer channels as needed. Also, optical fibers 39 or the like can extend through barrel 32 to transmit light or other energy from a proximal source to the body cavity of a patient. A shaft of needle driver 40 and a shaft of needle catcher 40' extend through channel 38b. Barrel 32 extends distally beyond inner sleeve 35 and intermediate sleeve 33.

A distal end of barrel 32 can be blunt as shown, tapered, beveled, slotted or chamfered as desired or have any other suitable distal configuration. Preferably, barrel 32 is made of a substantially cylindrical length of a substantially rigid material, such as stainless steel or some other medically acceptable plastic or metal material. Inner sleeve 35 defines a central channel through instrument 30 and terminates at proximal aperture 100 that includes, for example, a Luer lock, for connection with sources of fluid or suction, operating units, medical instruments and accessories, and a valve as shown in FIG. 1.

Needle driver 40 and needle catcher 40' each include a pair of cooperating needle holding members mounted for rotation along arcuate paths within annular channel 38b and for distal and proximal movement. The needle holding members of each needle holder are movable relative to one another to selectively grasp and release a suture needle during suturing procedures.

Figure 3A:
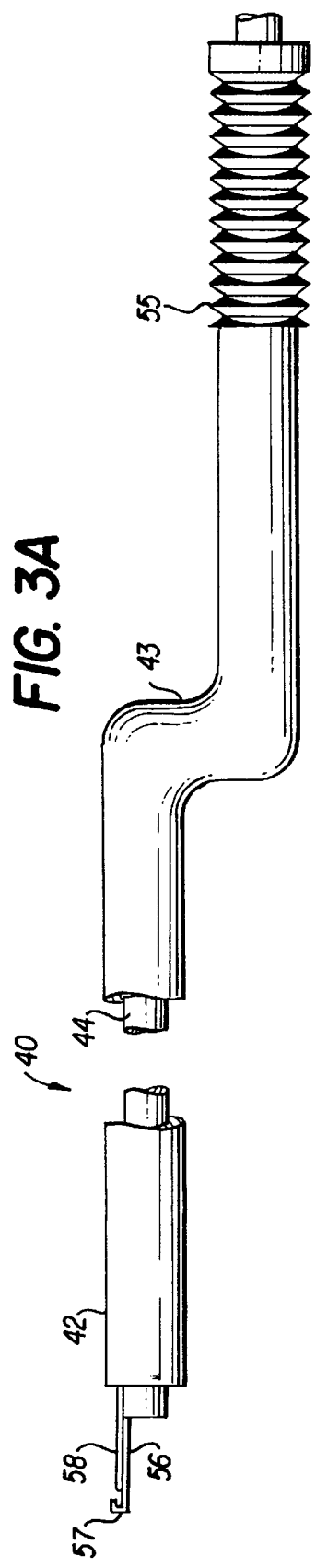
FIG. 3A illustrates a needle driver or first needle holder.

As best seen in FIG. 3A which illustrates needle driver 40 removed from barrel 32 needle driver 40 has a shaft constituted of tubular outer member 42 and tubular inner member 44 extending through outer member 42. Inner member 44 and outer member 42 define a shaft of needle driver 40 having bent portion 43, the significance of which will become apparent below. Inner member 44 and outer member 42 need not be tubular. However, the tubular configuration defines an additional operating channel that can be coupled to proximal aperture 101 (see FIG. 1) and used for insertion of instruments, aspiration, or other purposes. Needle holding members 56 and 58 of needle driver 40 are each formed of a rigid, semi-rigid or flexible strip of medically acceptable material, such as stainless steel, with each of the strips having an appropriate thickness and width to permit sliding movement of the needle holding members relative to one another. Needle holding member 56 is secured to the distal end of tubular inner member 44 and has hook 57 suitable for receiving the shaft or body of a suture needle.

Figure 3B:
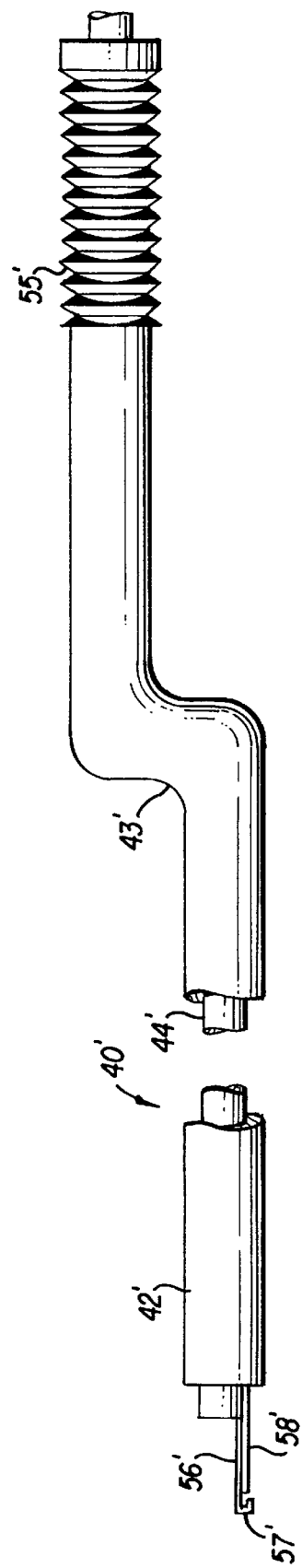
FIG. 3B illustrates a needle driver or first needle holder.

Needle holding member 58 is disposed on a distal end of tubular outer member 42 and includes a distal end adapted to fit within the mouth of hook 57 as a keeper, the distal end of needle holding member 58 preferably having a scalloped edge with one or more curved recesses to fit conformally against and frictionally engage a suture needle held within the mouth of the hook with added security. Needle catcher 40' is constructed similarly and includes needle holding members 56' and 58' as illustrated in FIG. 3B in which similar elements are labeled with like reference numerals and the suffix "'".

As noted above, inner member 44 and outer member 42 constitute a shaft of needle driver 40, and inner member 44' and outer member 42' constitute a shaft of needle catcher 40'. The shafts extend through barrel 32 to proximal controls 60. Collars 55 and 55' are disposed respectively on outer members 42 and 42' for reasons which will become apparent below. As illustrated in FIG. 1, proximal controls 60 of the preferred embodiment include two sets of scissor type handles 62 and 64 and 62' and 64' extending out of housing 79 disposed on barrel 32. The handles can be pivoted towards one another to cause relative movement of the associated pair of needle holding members of needle driver 40 and needle catcher 40' respectively. Button 66 (see FIG. 4) serves to selectively disengage handle 62 and 64 from needle driver 40 and permits handles 62 and 64 to be rotated in concert to a desired orientation, as indicated by arrow C in FIG. 1, without effecting the status of the needle holding members. This permits the surgeon to orient handles 62 and 64 in a desired manner before or during surgery. Button 66' serves a similar function with respect to handles 62' and 64'. Proximal controls 60 also include knobs 152 and 153, the purpose of which will be described below.

Figure 4:
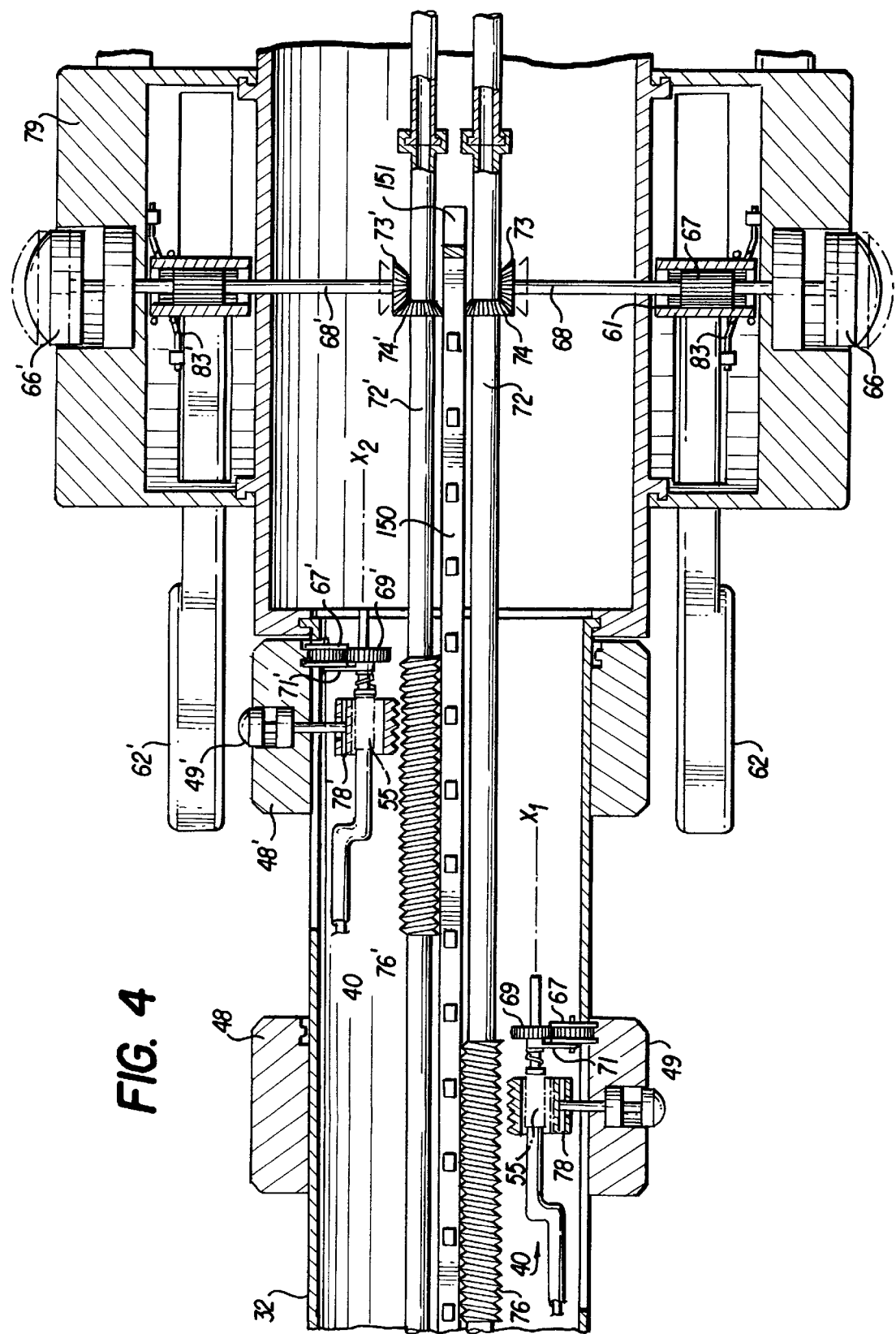
FIG. 4 illustrates the proximal controls in cross-section taken along line 4—4 of FIG. 1.

FIG. 4 illustrates the internal mechanism coupling proximal controls 60 to needle driver 40. Handles 62 and 64 are biased apart from one another by biasing member 83. A top portion of handle 62 is received in housing 79 and has aperture 61 formed therein. Gear 67 is slidably received in aperture 61 and engages with teeth formed on an inner surface that defines aperture 61. Gear 67 is disposed on shaft 68 coupled to button 66. Beveled gear 73 is also disposed on shaft 68. When push button 66 is pressed once, and released, it moves downward in FIG. 4 from the position illustrated by the dotted line to the position illustrated by the solid line. Pressing and releasing button 66 again will return button 66 to the position indicated by the dotted line. Of course, shaft 68, gear 67, and beveled gear 73 move along with button 66.

When button 66 is in the position illustrated by the solid line in FIG. 4, beveled gear 73 is engaged with beveled gear 74 mounted on shaft 72. Therefore, in this position, pressing handle 62 toward handle 64 causes shaft 72 to rotate. When button 66 is in the position illustrated by the dotted line, beveled gear 73 is not engaged with beveled gear 74 to permit handles 62 and 64 to be rotated to a desired orientation without affecting operation of instrument 30.

Button 49 is mounted in knob 48 and operates in a manner similar to button 66. However, operating member 78 is disposed on a stem of button 49. Operating member 78 is essentially cylindrical and has outer gear teeth adapted to be engaged with helical gear 76 disposed on shaft 72 and inner gear teeth adapted to be engaged with teeth of collar 55 disposed on a distal end of needle driver 40 as described above. When button 49 is in the position illustrated in FIG. 5, operating member 78 is engaged with helical gear 76 and with collar 55. Accordingly, in this position, rotation of shaft 72 in response to movement of handles 62 and 64 towards one another causes operating member 78 to move proximally along helical gear 76 thus causing outer member 42 to move proximally with respect to inner member 44. Proximal movement of outer member 44, with respect to inner member 42, causes outer member 44 to move needle holding member 56, the keeper, out of hook 57 on needle holding member 58. Conversely, releasing handle 62 causes operating member 78, and thus outer member 42, to move distally, due to the force of biasing member 83, thus forcing the keeper into the hook. Therefore, when buttons 66 and 49 are moved inward, compression of handles 62 and 64 causes the needle holding members of needle driver 40 to assume an open position. Note that spring 80 biases outer member 42 in the distal direction to normally bias the needle holding members into the closed position even when needle driver 40 is not engaged with handles 62 and 64. Also, there is adequate clearance between inner member 44 and outer member 42 at bent portion 43 to permit the relative movement. Alternatively, a portion of inner member 44 can be flexible to permit this movement.

Proximal controls 60 also include knobs 48 and 48' for causing rotational movement and linear movement of needle driver 40 and needle catcher 40' respectively. Gear 67 extends through slot S1 formed in barrel 32 and is engaged with gear teeth formed on knob 48 and gear 69 disposed on inner member 44. When knob 49 is pressed and released once to permit operating member 78 to move upward in FIG. 5, operating member 78 is no longer engaged with helical gear 76 or collar 55. In this position, rotation of knob 48 will cause inner member 42 to rotate due to gears 67 and 69. Outer member 42 can be keyed to inner member 44 to rotate along with inner member 44. Accordingly, rotation of knob 48 causes the rotation of proximal portions of the shaft of needle driver 40 about axis $X_1$ and thus causes needle holding members 56 and 58 to move through an arcuate path due to bent portion 43 formed in the shaft. Also, knob 48 is coupled to inner member 44 and outer member 42 by support assembly 71 which supports gears 67 and 69. Therefore, sliding knob 48 along slot S1 in proximal and distal directions will cause needle driver 40 to also move linearly in proximal and distal directions. Note that when button 49 is pressed and released again, operating member 78 is engaged with both helical gear 76 and collar 55 to prevent proximal and distal movement of needle driver 40. Unintentional rotation of needle driver 40 can be prevented by frictional contact or alternatively, a locking pin or the like can be provided to prevent unintentional rotation of knob 48 and needle driver 40.

To rotate needle driver 40 and cause arcuate movement of the needle holding members, the surgeon presses and releases button 49 so that button 49 is moved upward. This unlocks knob 48 and permits rotation of knob 48. Then, the surgeon rotates knob 48 to thus rotate gears 67 and 69 and inner member 44. Outer member 42 can be caused to rotate with inner member 44 by frictional contact, splines, or the like. As noted above, rotation of the shaft of needle driver 40 causes needle holding members 56 and 58 of needle driver 40 to move arcuately through slot 38b.

Proximal controls 60 of the preferred embodiment also include handles and 62' and 64' extending out of housing 79 which operate in a manner similar to handles 62 and 64. Button 66' serves to selectively disengage handle 62' and 64' from needle catcher 40' and permits handle 62' and 64' to be rotated in concert to a desired orientation without effecting the status of the needle holding members of needle catcher 40'. This permits the surgeon to orient handles 62' and 64' in a desired manner before or during surgery.

As illustrated in FIG. 4, handles 62' and 64' are biased apart from one another by biasing member 83'. A top portion of handle 62' is received in housing 79 and has aperture 61' formed therein. Gear 67' is slidably received in aperture 61' and engages with teeth formed on an inner surface that defines aperture 61'. Gear 67' is disposed on shaft 68' which is coupled to button 66'. Beveled gear 73' is also disposed on shaft 68'. When push button 66' is pressed once, and released, it moves upward in FIG. 4 Pressing and releasing button 66' again will return button 66' to the position indicated by the dotted line. Of course, shaft 68', gear 67', and beveled gear 73' move along with button 66'.

When button 66' is in the position illustrated by the solid line in FIG. 4, beveled gear 73' is engaged with beveled gear 74' mounted on shaft 72'. Therefore, in this position, pressing handle 62' toward handle 64' causes shaft 72' to rotate. When button 66' is in the position illustrated by the dotted line, beveled gear 73' is not engaged with bevel gear 74' to permit handles 62' and 64' to be rotated to a desired orientation without affecting operation of the instrument.

Operating member 78' is disposed on a stem of button 49'. Operating member 78' is essentially cylindrical and has outer gear teeth adapted to be engaged with helical gear 76' disposed on shaft 72' and inner gear teeth adapted to be engaged with teeth of collar 55' disposed on a distal end of needle catcher 40'. When button 49' is in the position illustrated in FIG. 4, operating member 78' is not engaged with helical gear 76' and collar 55'. However, when button 49' is pressed and released once, these elements are engaged and, in this position, rotation of shaft 72 in response to movement of handles 62' and 64' towards one another causes operating member 78' to move proximally along helical gear 76' thus causing outer member 42' to move proximally with respect to inner member 44'. Proximal movement of outer member 44', with respect to inner member 42', causes needle holding member 56', i.e. the keeper, to move out of hook 57' on needle holding member 58'. Conversely, releasing handle 62' causes operating member 78', and thus outer member 42' to move distally, due to the force of biasing member 83', thus permitting needle holding members 56' and 58' to return to the normally closed position. Therefore, when buttons 66' and 49' are moved inward, compression of handles 62' and 64' causes the needle holding members of needle catcher 40' to open. Note that spring 80' biases outer member 42' in the distal direction to normally bias the needle holding members into the closed position even when needle driver 40' is not engaged with handles 62' and 64'. Also, there is adequate clearance between inner member 44' and outer member 42', or inner member 44 is flexible, at bent portion 43' to permit the relative movement discussed above.

As noted above, knob 48' causes rotational movement and linear movement of needle driver 40'. Gear 67' extends through slot S2 formed in barrel 32 and is engaged with gear teeth formed on knob 48' and gear 69' disposed on inner member 44'. When knob 49' is pressed and released, operating member 78' is not engaged with helical gear 76' or collar 55'. In this position, rotation of knob 48' will cause inner member 42' to rotate due to gears 67' and 69'. Outer member 42' can be keyed to inner member 44' to rotate along with inner member 44'. Accordingly, rotation of knob 48' causes distal portions of the shaft, which are offset by bent portion 43, to move through groove 38b in an arcuate path. Also, knob 48' is coupled to inner member 44' and outer member 42' by support assembly 71' which supports gears 67' and 69'. Therefore, sliding knob 48' along slot S2 in proximal and distal directions will cause needle catcher 40' to also move linearly in proximal and distal directions. Note that when button 49' is pressed and released again, operating member 78' is engaged with both helical gear 76' and collar 55' to prevent proximal and distal movement of needle driver 40'. Unintentional rotation of needle catcher 40' can be prevented by frictional contact or alternatively, a locking pin or the like can be provided to prevent unintentional rotation of knob 48' and needle catcher 40'.

Pusher member 150 extends through barrel 32 from a proximal end, at which knob 152 (see FIG. 1) is mounted, to a distal end, and extends to a position opposite needle dispensing cartridge 200 as described below. Knob 152 extends out of housing 79 to permit the surgeon to slide pusher member 150 distally through barrel 32. Also, pusher member 151 extends through barrel 32 from a proximal end, at which knob 153 (see FIG. 1) is mounted, to a distal end, and extends to a position opposite needle collecting cartridge. Knob 153 extends out of a lower portion of housing 79 in FIG. 1.

Needle holding members 56' and 58' of needle catcher 40' are shown as being identical to the needle holding members 56 and 58 of the needle driver 40. However, it will be appreciated that the needle driver and the needle catcher can be of different configurations dependent upon procedural use and other considerations such as cost. For example, one or both of the needle drivers and needle catchers can be fixed rotationally in barrel 32 and moved arcuately by rotating barrel 32.

As shown in FIG. 2, needle dispensing cartridge 200 is disposed in channel 38a near a proximal end of barrel 32. A retaining device, such as a pin and recess configuration (not illustrated), retains needle dispensing cartridge 200 in position in barrel 32 while permitting needle dispensing cartridge 200 to be removed and replaced with another cartridge from the distal end. Similarly, needle collecting cartridge 300 is disposed in channel 38a near a proximal end of barrel 32, at a position angularly displaced from needle dispensing cartridge 200. In the preferred embodiment, the two cartridges are in opposition to one another. However, the cartridges can be positioned in any desired manner. A retaining device, such as a pin and recess configuration (not illustrated), retains needle collecting cartridge 300 in position in barrel 32 while permitting needle collecting cartridge 300 to be removed and replaced with another cartridge from the distal end.

Needle dispensing cartridge 200 is best illustrated in FIGS. 5A–5F and includes housing 202 containing support plate 204 and sliding member 206. Support plate 204 has an arcuate upper surface on which needle holding stations 208a, 208b, and 208c are defined by raised portions having a recess therebetween. Of course, there can be more or less than three needle holding stations. Also, the needle holding stations can be much closer together than in the illustrated embodiment, which spacing is chosen for clarity of illustration. Further, needle holding stations 208a–208c can be of any configuration that temporarily secures needles at the desired position which will become apparent from the description below. When needle dispensing cartridge 200 is initially loaded, needles N1–N3 are disposed on support plate 204 at needle holding stations 208a–208c respectively. Resilient material 210, made of a nonabsorbent coated biocompatible rubber or the like, is disposed on an inside upper surface of housing 200 to press needles N1–N3 toward support plate 204 to retain needles N1–N3 in the desired positions.

Sliding member 206 is disposed in housing 202 below support plate 204 to be slidable with respect to support plate 204. Pins 212 extending from sliding member 206 are slidingly disposed in cam slots 214 formed on a lower portion of support plate 204. Cam slots 214 define the path of movement of sliding member 206. Push members 220a, 220b, and 220c extend upward from sliding member 206 through slot 218 formed in a central portion of support plate 204. In the rest position, or initial position, illustrated in FIG. 5C, push members 220a–220c are respectively positioned just behind needle positioning stations 208a–208c, which hold needles N1–N3. Note that the top portion of housing 202 of needle dispensing cartridge 200 can be separated from other portions of housing 202 at pressure fitting joints 230 to facilitate loading of needles N1–N3 in needle dispensing cartridge 200 prior to use. Cartridge 200 is illustrated with the top portion of housing 202 removed in FIG. 5A.

Prior to use in a procedure, needle dispensing cartridge 200 is loaded into a distal end of barrel 32 by pushing needle dispensing cartridge 200 into channel 38a until needle dispensing cartridge is retained by the retaining device or any other detent device. In this position, a distal end of pusher member 150 enters a slot formed in the rear wall of housing 202 to oppose abutment surface 207 formed on a rear portion of sliding member 206. This permits the surgeon to cause sliding member 206 to slide forward along groove 214 by sliding knob 152 of proximal controls 60.

Figure 5C:
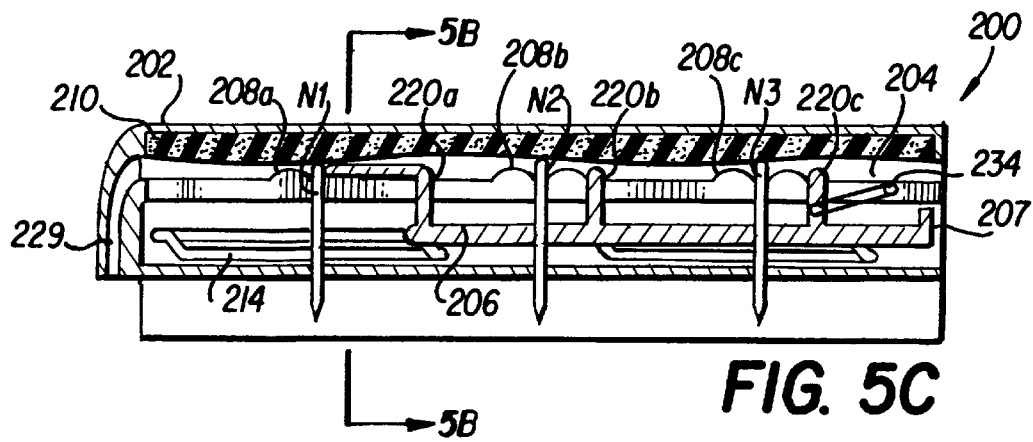
FIG. 5C illustrates the needle dispensing cartridge in cross-section, taken along line 5C—5C in FIG. 5A, in the initial position before ejecting a needle.
Figure 5D:
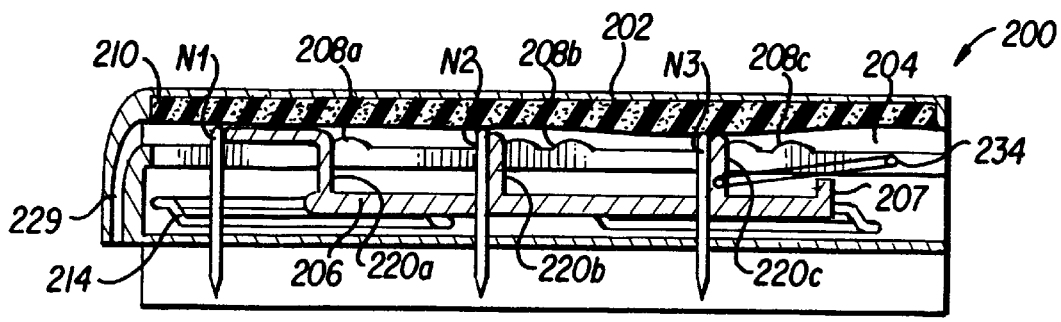
FIG. 5D illustrates the needle dispensing cartridge in cross-section, taken along line 5C—5C in FIG. 5A, as needles are pushed forward.
Figure 5E:
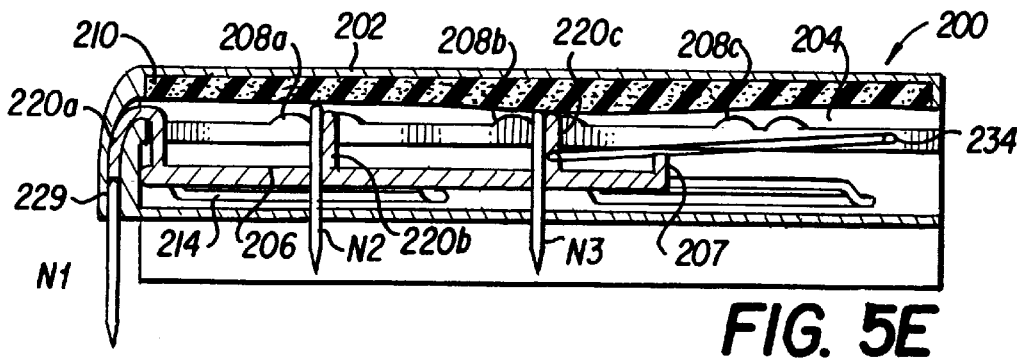
FIG. 5E illustrates the needle dispensing cartridge in cross-section, taken along line 5C—5C in FIG. 5A, as a needle is ejected.

After instrument 30 has been inserted into an anatomical cavity, through a portal sleeve or the like, and when a needle is to be dispensed from needle dispensing cartridge to be grasped by a needle holder for a suturing procedure, the surgeon slides knob 152 forward to thereby cause pusher member 150 to move distally and sliding member 206 to move forward, i.e. distally, along an upper portion of groove 214. Note that a distal end of pusher member 150 abuts abutment surface 207 of sliding member 206. This movement of sliding member 206 causes push members 208a–208c to push needles N1–N3 forward respectively as illustrated in FIG. 5D. When sliding member 206 is pressed fully forward in groove 214, push member 208a pushes needle N1 out of channel 229 formed in housing 202 as illustrated in FIG. 5E. Note that push member 208a includes a flexible extension that conforms to channel 209. Travel of the flexible extension through channel 209 insures that the foremost needle is positively ejected from housing 202 regardless of its orientation. This permits needle N1 to be loaded into a needle holder in the manner described in greater detail below regardless of the orientation of instrument 30. The length of the flexible extension can be varied to properly eject a needle.

Figure 5F:
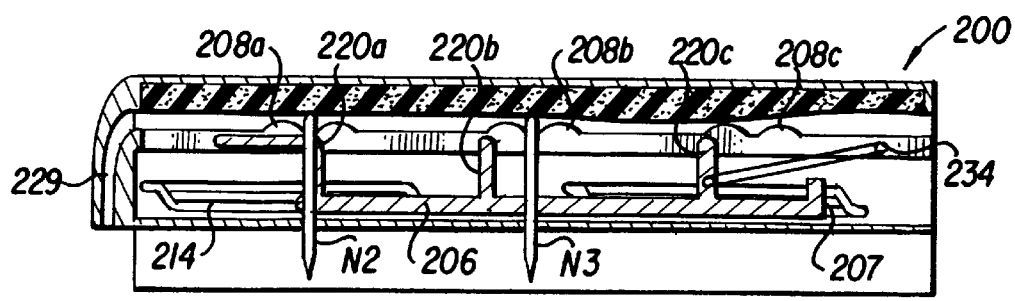
FIG. 5F illustrates the needle dispensing cartridge in cross-section, taken along line 5C—5C in FIG. 5A, as the sliding member returns to the initial position.

Simultaneously, needle N2 is pushed forward along support plate 204 to needle holding station 208a by push member 220b and needle N3 is pushed forward along support plate 204 to needle holding station 208b by push member 220c as illustrated in FIG. 5E. Note that biasing member 234 biases sliding member 206 proximally toward a rear portion of housing 202 into the initial position shown in FIG. 5C. Also, the biasing force of biasing member 234 biases pusher member 150 proximally. Alternatively, an additional biasing member can be coupled to pusher member 150. Therefore, when the surgeon releases knob 152, sliding member 204 returns toward a rear portion of housing 202, i.e. moves proximally. However, guide members 234a and 234b are disposed in groove 214 to force pins 212 to travel through a lower portion of groove 214 when sliding member 206 moves toward the rear of housing 202. This causes sliding member 206 and push members 208a–208c to move downward when returning to the initial position as illustrated in FIG. 5F. This downward movement causes push members 208a–208c to pass below needles N2 and N3 when sliding member 206 returns proximally to the initial position thereby not disturbing needles N2 and N3. Therefore, pushing knob 152 distally and releasing knob 152 causes a needle in the foremost needle station to be ejected from needle dispensing cartridge 200 and causes all the remaining needles to advance forward by one needle holding station. Channel 211 can be defined in housing 202 to accommodate suture material attached to the needles (see FIG. 5B).

Figure 6A:
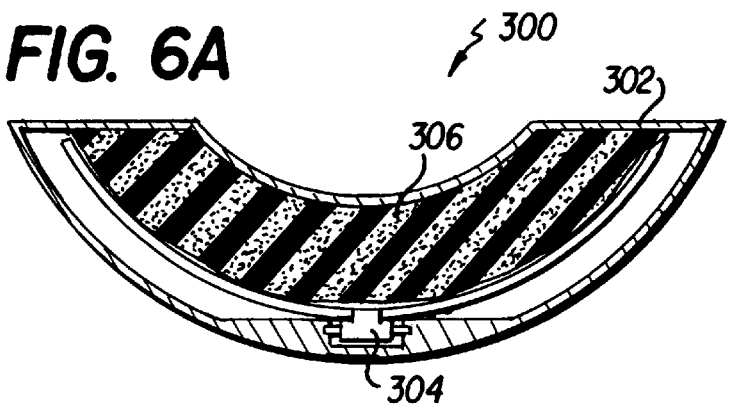
FIG. 6A illustrates the needle collecting cartridge in cross-section taken along line 6A—6A in FIG. 6B.
Figure 6B:
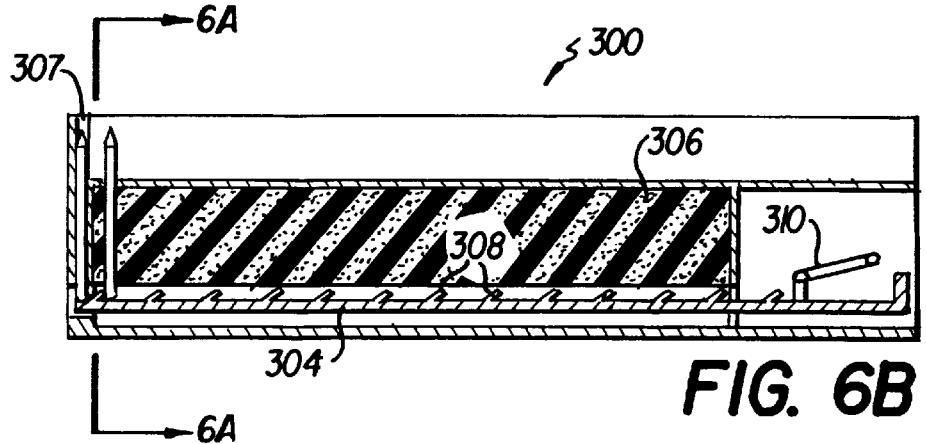
FIG. 6B illustrates the needle collecting cartridge in cross-section when a needle collecting cartridge in cross section when a needle is dropped therein.

Needle collecting cartridge 300 is illustrated in FIGS. 6A–6D and includes housing 302 having slide member 304. Resilient material 306 is disposed on an upper inside surface of housing 32, as viewed in the drawing, to press needles toward slide member 304. Housing 302 has channel 307 formed in a front, i.e. distal, portion to receive needles. Slide member 304 is slidable in housing 302 from the proximal position illustrated in FIG. 6B to the distal position illustrated in FIG. 6C, at which a distal end of slide member 304 extends through an opening in housing 302. As illustrated in FIG. 6B, a used needle can be dropped into channel 307 by needle holding members of needle driver 40 or needle catcher 40'. A magnetic element can be associated with channel 306 to positively draw a needle into channel 306. Once a needle is seated in channel 306, knob 153 is advanced distally to push sliding member 304 distally with pusher member 151.

Figure 6C:
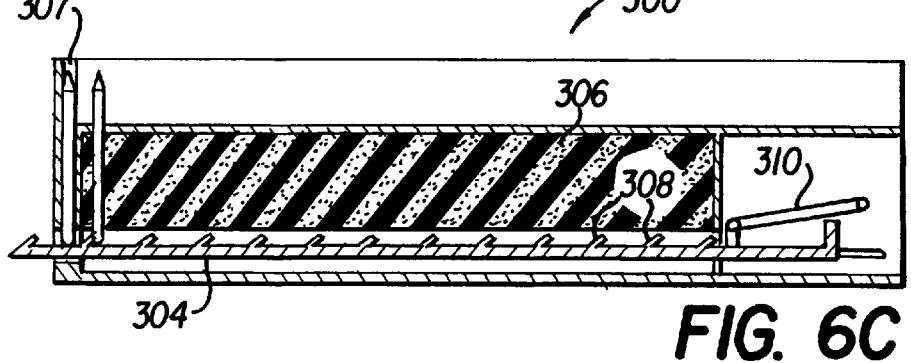
FIG. 6C illustrates the needle collecting cartridge in cross-section with the sliding member advanced.
Figure 6D:
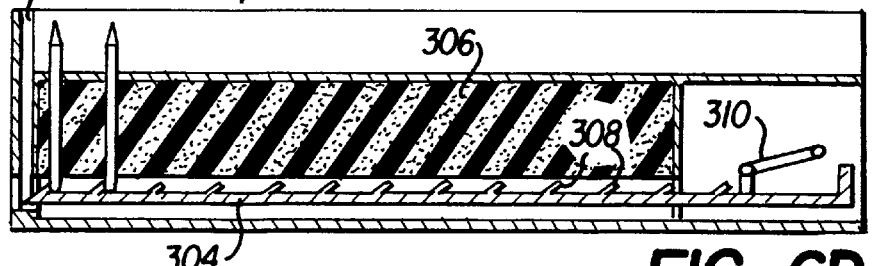
FIG. 6D illustrates the needle collecting cartridge with the slide member retracted after collecting a needle.

Sliding member 304 has angled fingers 308 formed thereon which slide under the needle in channel 307 as sliding member 304 is advanced distally as seen in FIG. 6C. However, when sliding member 304 returns to the proximal position, due to the force of biasing member 310, the foremost of fingers 308 pulls the needle out of channel 307 into the main portion of housing 302 as seen in FIG. 6D. Also, needles in the main portion are advanced proximally in a similar manner. Therefore, pushing knob 153 forward and releasing it will cause a needle received in channel 307 to be drawn into housing 302 and will advance needles in housing 302 proximally.

In use, instrument 30 is grasped using proximal controls 60 and, in the case of an endoscopic procedure, the instrument is guided to the operative site through a portal sleeve positioned in the wall of an anatomical cavity. The portal sleeve can be positioned in the anatomical cavity wall using any suitable penetrating technique, including those creating puncture sites by means of removable obturators, such as trocars, and can include a valve housing, if desired, to prevent loss of pneumoperitoneum during insertion and withdrawal of the instrument. Visualization of the endoscopic procedure can be accomplished using a conventional endoscope, or other imaging instrument, incorporated into the instrument, for example within operating channel 38c, or separately positioned within the anatomical cavity through a second portal sleeve located at another puncture site.

Figure 7:
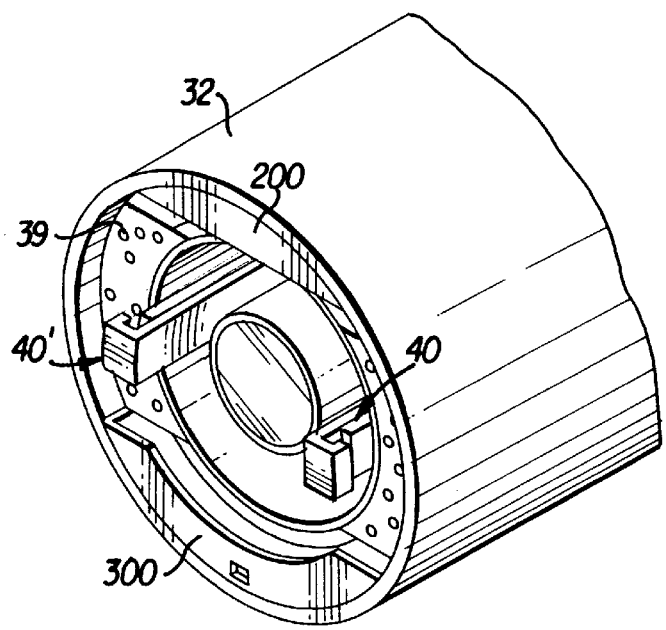
FIG. 7 illustrates the distal end of the preferred embodiment in an insertion or protected position.

Prior to insertion, needle driver 40 and needle catcher 40' are preferably initially positioned at diametrically opposed locations within annular channel 38b as illustrated in FIG. 7. Also, needle driver 40 and needle catcher 40' can be moved proximally to be protected by a distal end of barrel 32 which extends beyond the distal ends of needle holders 40 and 40'. This facilitates insertion into the body cavity. Alternatively, a retractable protective member can be provided over the distal end of barrel 32. Prior to a suturing operation, a curved suture needle N of substantially semi-circular configuration is positioned in needle driver 40 by moving the needle holding members 56 and 58 to the open position, placing needle N in the mouth of hook 57, ejecting needle N from needle dispensing cartridge 200, and moving the needle holding members to the closed position to hold the suture needle in place.

Figure 8:
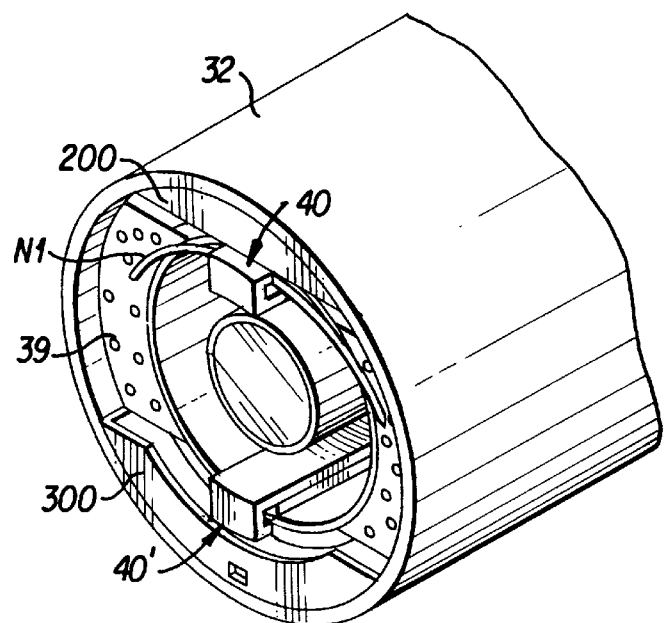
FIG. 8 illustrates the distal end of the preferred embodiment as a needle is loaded into a needle holder.
Figure 8:
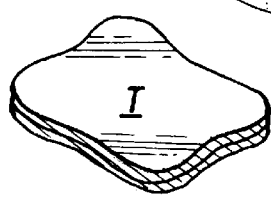
Figure 9:
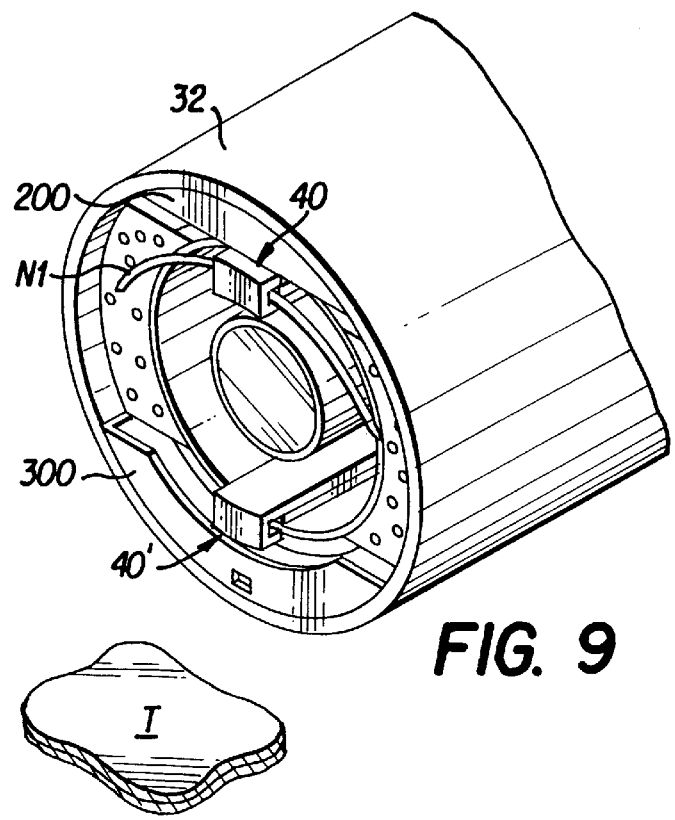
FIG. 9 illustrates a distal end of the preferred embodiment after a needle has been loaded and grasped.

Needle holding members 56 and 58 are moved to the open position by compressing handles 64 and 66, such that a distal end of needle holding member 58 is moved proximally relative to hook 57. Needle N is then placed in the mouth of hook 57 by ejecting a needle from needle dispensing cartridge 200 in response to advancement of knob 152 as illustrated in FIG. 8. Of course needle driver 40 is moved proximally or distally by sliding knob 48 to align an opening of hook 57 with an opening of channel 209 formed in needle dispensing cartridge 200 during the needle dispensing operation. Stops or other indexing devices can be provided to facilitate this alignment. With needle N positioned within hook 57 of needle driver 40, handles 64 and 66 are released to cause a distal end of needle holding member 58 to move distally relative to hook 57 and into contact with the body of needle N as shown in FIG. 9. Needle N is thus loaded and held securely between needle holding members 56 and 58 and will thus move arcuately with needle driver 40 during the suturing procedure.

Prior to suturing, needle catcher 40' is configured to receive the tip of the suture needle by moving needle holding members 56' and 58' to the open position prior to, during or after the suture needle has been loaded in needle driver 40 in the manner described above. This is accomplished by compressing handles 62' and 64'. Note that lock projections 63' and 65' permit handles 62' and 64' to be retained in the open position.

Figure 10:
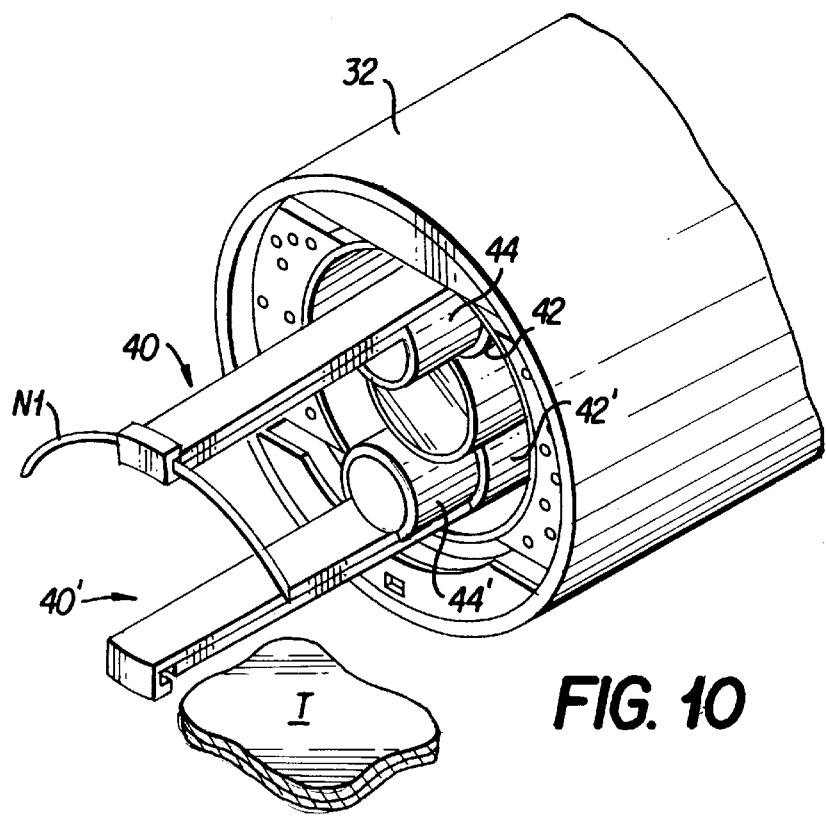
FIG. 10 illustrates a distal end of the preferred embodiment in a suturing position.
Figure 11:
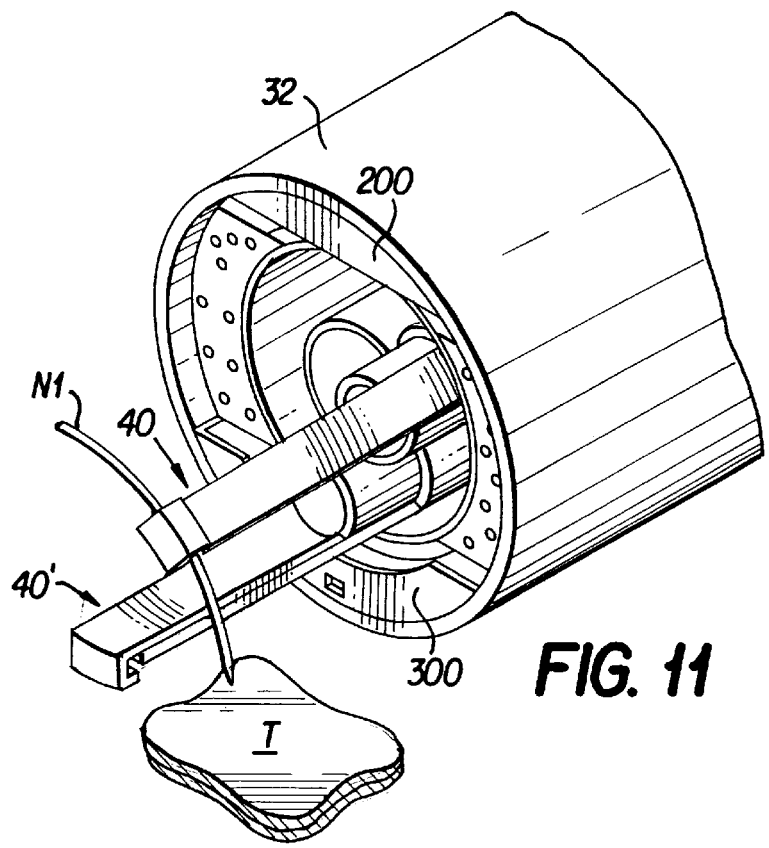
FIG. 11 illustrates a distal end of the preferred embodiment as a needle holder begins to push the needle through tissue.
Figure 12:
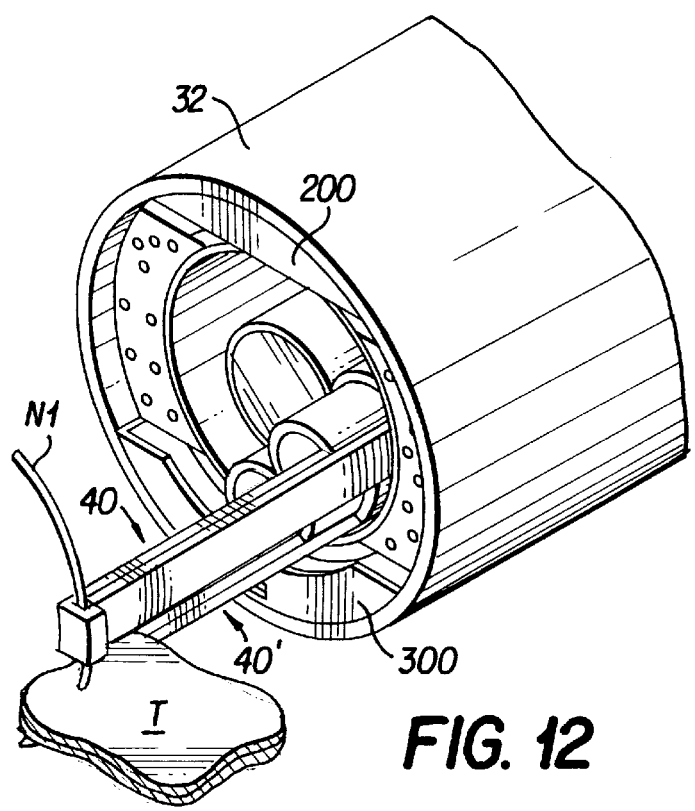
FIG. 12 illustrates a distal end of the preferred embodiment with the needle penetrating tissue.

Referring now to FIG. 10, instrument 30 is manipulated so that anatomical tissue T (only a portion of which is illustrated), which is to be sutured, is positioned between the tip of needle N and needle catcher 40' with a length of suture material being shown attached to the shank end of needle N. Using needle catcher 40' as a backing or support for the tissue, the needle is driven through tissue T and into needle catcher 40' by rotating knob 48 in a clockwise direction. Needle N is thus caused to penetrate through the anatomical tissue T along an arcuate path having a radius of curvature approximately equal to or commensurate with the radius of curvature of the needle until needle N is disposed between needle holding members 56' and 58' of needle catcher 40' as shown in FIGS. 11 and 12.

With needle N positioned in needle catcher 40', handles 62' and 64' are released causing a distal end of needle holding member 58' to contact the body of suture needle N to retain needle N between hook 65' of needle holding member 56' and the distal end of needle holding member 58'. Handles 62 and 64 can then be compressed thereby moving the distal end of needle holding member 58 proximally relative to hook 57 of needle holding member 56 to release needle N from needle driver 40.

Figure 13:
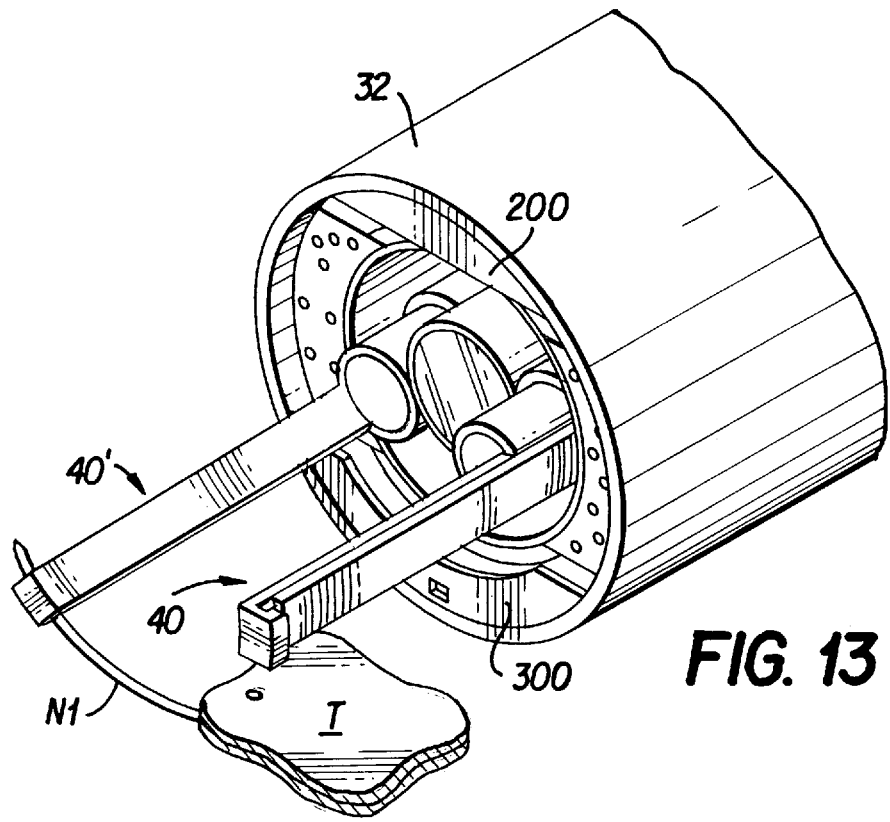
FIG. 13 illustrates a distal end of the preferred embodiment as the needle is pulled through tissue.

With needle N secured within needle catcher 40', knob 48' is rotated clockwise, and needle N is thus pulled through the anatomical tissue with the length of suture material as illustrated in FIG. 13. Knob 48 can then rotated in a counterclockwise direction about 180°, to allow the tip of needle N to be received in needle driver 40 again. Next the handles are manipulated to open the needle holding members of needle catcher 40' and to close the needle holding members of needle driver 40.

A second stitch can optionally be made by moving suturing instrument 30 slightly relative to tissue T and rotating knob 48 to cause the tip of needle N to penetrate through the tissue at a second location. Needle catcher 40' has preferably previously been rotated by rotation of knob 48' to receive the suture needle, after which handles 62' and 64' are released to secure needle N within needle catcher 40'. At about the same time, handles 62 and 64 are compressed to permit the suture needle to be pulled completely through the tissue by rotation of needle catcher 40'. At this point, needle N may have to be advanced circumferentially in order for the tip to protrude sufficiently from the needle catcher for additional stitches to be formed. Such repositioning can, for example, be accomplished by grasping the proximal end of the needle with a separate needle holding instrument and releasing the needle holding members to allow manipulation of the needle to a position in needle driver 40 wherein the tip of the needle protrudes sufficiently to pass through the anatomical tissue and be captured by the needle catcher 40' or by pressing the shank of needle N against a retractable needle pusher.

At any point during the operative procedure, operating channel 38c of the suturing instrument can be used for irrigation or aspiration and can serve as a space for holding the suture material or as a portal for the introduction of other medical instruments such as, for example, forceps, cutting members and endoscopes.

When needle N has been passed through tissue T the desired number of times needle catcher 40' or needle driver 40 is manipulated to pass needle N through a loop defined by a knot in the suture material. The knot can then be pulled tightly against tissue T and the suture material can be separated from needle N by cutting the suture material. For example, notch 59 can be formed in needle holding member 56, as shown in FIGS. 8 and 10, and a sharp edge can be defined on a distal end of needle holding member 58. This arrangement can cut the suture material by placing the suture material in notch 59 and advancing needle holding member 58 distally.

If desired, knotting elements can be used in lieu of traditional knotting techniques during the suturing procedure. Some examples of suitable knotting elements for this purpose are described in pending applications Ser. Nos. 08/366,285, filed Dec. 29, 1994; 08/377,723, filed Jan. 25, 1995; 08/401,002, filed Mar. 9, 1995; and 08/585,875, filed Jan. 16, 1996, the disclosures of which are incorporated herein by reference. In addition, if opposite axial ends of suture needle N are provided with sharp, tissue penetrating tips, it is possible to penetrate the anatomical tissue T at multiple locations in order to form a continuous run of stitches merely by passing the needle back and forth through tissue in a shuttle manner.

Figure 14:
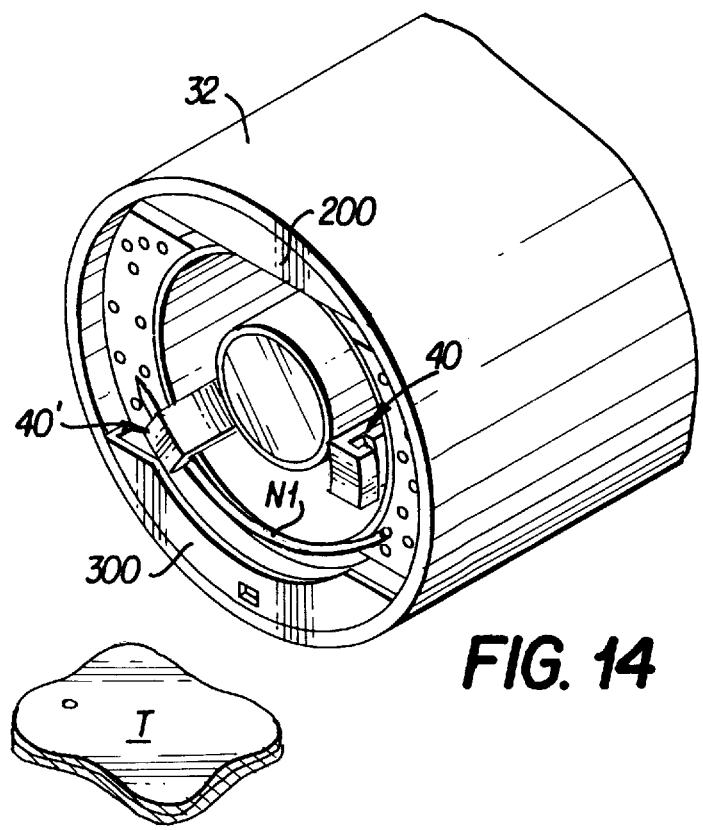
FIG. 14 illustrates the distal end of the preferred embodiment in a needle collecting position.

When suturing is completed, needle catcher 40' is rotated and moved proximally to a position at which the needle opposes an opening of channel 307, as illustrated in FIG. 14, and needle holding members 56' and 58' are opened to drop the needle into channel 307. Subsequently knob 153 is pushed distally and released to draw the needle into needle collecting cartridge 300 in the manner described above. The needle can be drawn into channel 307 by gravity if needle collecting cartridge 300 is positioned below the needle. Alternatively the needle can be drawn into channel 307 by a magnetic member disposed in cartridge 300 or by a grasping device that pulls the needle out of needle catcher 40'. Also, the needle can be drawn out of needle driver 40 in a similar manner. Further suturing procedures can be accomplished without withdrawing instrument 30 and without introducing a separate needle loading instrument by repeating the procedures described above.

From the above, it will be appreciated that the suturing instrument according to the present invention permits multiple suturing procedures during endoscopic or open surgery without the need for multiple needle holding instruments inserted through multiple puncture sites and without the need for withdrawing the instrument to reload the needle.

The needle driver and the needle catcher of the suturing instrument can be of the same design or of different designs as long as each includes a needle holder capable of grasping and releasing a needle. Alternatively, a single needle holder can be used for suturing with or without a support member placed behind the tissue. The needle holders can be configured to hold any type of needle including, but not limited to, straight and curved needles and are preferably mounted to permit movement of the needle holders relative to one another in directions causing the needles to be passed from one needle holder to the other. In the case of curved needles, the needle holders are preferably mounted for rotation about a longitudinal axis of the suturing instrument in an arcuate path having a radius of curvature substantially commensurate with the radius of curvature of the needle. For straight needles, one or both of the needle holders is preferably pivotable away from a longitudinal axis of the suturing instrument and the needles are preferably held by the needle holders such that tissue penetrating tips of the needles are oriented toward the longitudinal axis of the instrument. The needle holders can have any of the configurations disclosed in the related applications, for example.

One or more lengths of suture material can be attached to each suture needle at any desirable location along the body or tip of the needle including, but not limited to, the proximal end of the needle, intermediate or medial portions of the needle body, or locations adjacent the tip of the needle. It will also be appreciated that the suturing instrument according to the present invention can be used with any type of standard suturing needle including, but not limited to, needles having sharp or blunt tissue penetrating tips, and needles having tissue penetrating tips at opposite axial ends of a needle body.

The needle dispensing and receiving cartridges can be any configuration that holds and dispenses or receives needles. For example, the needles can be dispensed and received by moving along a corkscrew member or the like. Also, the needles can be stored in the cartridges between two rack members and the needle holding members can be moved towards and away from the rack members to place the needle in, or pull the needle out of the rack members. Further, the needles can be flexed when stored in the cartridges to conserve space. The cartridges can be configured to dispense and receive the needles at any desired orientation depending on the structure of the needle holders. Alternatively, the needles can be housed directly in the barrel or other part of the instrument, such as the needle holders, without the need for removable cartridges.

The needle holding members of the needle catcher and the needle driver shown and described herein are exemplary of the types of needle holding members that can be used according to the present invention. Accordingly, the needle holding members can have any suitable configuration for cooperatively grasping needles to suture anatomical tissue including, but not limited to, configurations wherein the needle holding members pivot, slide or otherwise move relative to one another to capture and release a needle. The needle holding members can, for example, be of straight, curved or angled configuration and can provided with ribs, grooves, slots and/or holes along grasping surfaces to assure a positive grip. While the hooked needle holding member has been shown and described herein as being disposed radially outward of the straight needle holding member or keeper, it will be appreciated that the hooked member can be disposed radially inward of or circumferentially side-by-side with the keeper if desired. In such a case, the cartridges can be located radially inward of the needle holders to dispense and receive needles. Of course, the needle holding members can be of any of the configurations disclosed in the related applications cited above, for example.

The needle holding members can also carry cutting members, such as slots with sharp edges or protruding blades for cutting tissue or suture material, and can have opposed arcuate or concave portions for clamping tubular objects, such as organs, without compressing the objects. Also, there can be only one, or more than two, needle holders in the instrument. The needle holders can be movable or fixed relative to the barrel. If the needle holders are fixed, rotation can be accomplished by rotating the entire barrel. Also, the needle cartridges can be movable in the barrel to be aligned with fixed needle holders. The needle holders can be moved proximally and distally to facilitate tying knots in the suture material and cutting the suture material after suturing.

The needle driver and catcher of the present invention are preferably movably disposed about a tubular member defining a central channel or passage through the instrument to permit various medical devices and instruments such as, for example, needles, blades, forceps, cauteries, endoscopes, illuminating devices and lengths of suture material to be introduced at the operative site without the need of having to remove the suturing instrument from the body. Alternatively, the channel can be disposed eccentrically with respect to the barrel. The barrel and the tubular member defining the operating channel can have any configuration in transverse cross-section including, but not limited to, elliptical, polygonal and irregular cross-sectional configurations. Also, all or part of the inner surface of the tubular member can be electrically insulated to permit passage of electrosurgical instruments therethrough for cauterization procedures. The valves and couplings shown at the proximal end of the tubular members are merely exemplary of the types of conventional valves and conventional couplings that can be used.

The proximal controls shown and described herein are exemplary of the types of controls that can be used. However, the controls can be of any configuration. In particular, the mechanisms shown for operating the needle holding members of the needle catcher and the needle driver, for moving the needle catcher and needle driver relative to one another and for ejecting and receiving needles from the cartridges are merely exemplary of the types of mechanisms that can be used to perform these functions. For example, in the case of slidable needle holding members, mechanisms including, but not limited to, push-buttons with wedge-shaped members for engaging flanges carried by each member, resilient U-shaped members with arms connected to each member, and triggers connected to the members via linkages or gears can be used to move the needle holding members relative to one another. In the case of pivoted needle holding members or jaws, mechanisms such as, a tubular member movable relative to the jaws or linkages connecting one or both of the jaws with a trigger or the like at a proximal end of the instrument can be used move the needle holding member or jaws relative to one another.

The needle holding members can be biased to a normally open state or a normally closed state for grasping a suture needle, and can be provided with any type of locking feature to permit the surgeon to maintain the members in a desired position. Automatic controls can be provided in which all or part of a suturing operation is accomplished merely by operating the controls once, for example squeezing and releasing handles.

The components of the suturing instrument of the present invention can be made of any suitable, medical grade materials to permit sterilization for reuse or disposal for single patient use. The components can be made of multiple parts of various configurations and materials to reduce cost. The instrument can have various valves, stop cocks and seals therein to control the flow of fluid and medical devices through the suturing instrument. The needle collecting structure and function can be omitted and bioabsorbable needles, such as those disclosed in U.S. Pat. No. 4,981,149, can be used and left in the anatomical cavity after suturing. Further, the needles can be dispensed from, and collected in, the same cartridge or the same portion of the instrument.

The features of the various embodiments described above can be combined in any manner desired dependent upon the operational requirements of the procedure to be performed and the complexity of the suturing instrument. It will also be appreciated that the suturing instrument of the present invention can be used to apply single or multiple stitches in open or endoscopic procedures.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A suturing instrument comprising:
   at lease one needle holder;
   a needle dispensing mechanism configured to dispense a plurality of needles, one at a time, to said needle holder; and
   a needle collecting mechanism configured to collect needles from said needle holder, said dispensing mechanism and said collecting mechanism being integral with other portions of said instrument.

2. A suturing instrument as recited in claim 1, further comprising:
   an elongated barrel having proximal and distal ends, at least a portion of said needle holder extending from said distal end.

3. An instrument as recited in claim 2 wherein there are two needle holders.

4. An instrument as recited in claim 3, wherein at least one of said needle holders is movable relative to said barrel.

5. An instrument as recited in claim 3, wherein both of said needle holders are movable relative to said barrel.

6. An instrument as recited in claim 2, wherein said dispensing mechanism comprises a needle dispensing cartridge disposed in said barrel and adapted to loading needles in said at least one needle holder and said collecting mechanism comprises a needle collecting cartridge disposed in said barrel and adapted to collect needles from said at least one needle holder.

7. An instrument as recited in claim 3, wherein said needle dispensing mechanism comprises a needle dispensing cartridge disposed in said barrel and adapted to loading needles in one of said needle holders and said needle collecting mechanism comprises a needle collecting cartridge disposed in said barrel and adapted to collecting needles from the other of said needle holders.

8. An instrument as recited in claim 7, wherein said needle holders are moveable through an arcuate slot formed in said barrel and said needle dispensing cartridge and said needle collecting cartridge are located radially outward from said needle holders.

9. An instrument as recited in claim 8, wherein said needle holders are movable through an arcuate slot formed in said barrel and said needle dispensing cartridge and said needle collecting cartridge are located radially inward from said needle holders.

10. An instrument as recited in claim 8, wherein said needle holders are movable axially with respect to said barrel.

11. An instrument as recited in claim 9, wherein said needle holders are movable axially with respect to said barrel.

12. A suturing instrument as recited in claim 9, further comprising:
   a needle collecting mechanism configured to collect needles, said needle collecting mechanism being integral with other portions of said instrument.

13. An instrument as recited in claim 12, wherein said needle dispensing mechanism is disposed in said barrel.

14. An instrument as recited in claim 13, wherein said needle dispensing mechanism comprises a needle dispensing cartridge adapted to housing at least one needle and dispensing said at least one needle, one at a time, to said needle holder.

15. A suturing instrument comprising:
   at least one needle holder having;
   a needle dispensing mechanism containing a plurality of needles and configured to dispense at least one needle, one at a time, to said needle holder, said needle dispensing mechanism being integral with other portions of said instrument.

16. An instrument as recited in claim 15, further comprising:
   an elongated barrel having proximal and distal ends, at least a portion of said needle holder extending from said distal end.

17. A method of suturing anatomical tissue comprising:
   inserting a distal end of an instrument into an anatomical cavity;
   dispensing a needle from a first portion of the instrument;
   loading the needle into a needle holder of the instrument; and
   suturing tissue by manipulating the needle holder to pass the needle through the tissue.

18. A method as recited in claim 17, further comprising the step of:
   collecting the needle, after said suturing step, into a second portion of the instrument.

19. A method as recited in claim 18, wherein said suturing step comprises pulling the needle out of the needle holder with a needle catcher.

20. A method as recited in claim 18, wherein said suturing step further comprises moving the needle holder and the needle catcher through arcuate grooves formed in the barrel.

21. A method as recited in claim 18, wherein said dispensing step comprises dispensing the needle from a dispensing cartridge disposed in the instrument.

22. A method as recited in claim 18, wherein said collecting step comprises collecting the needle in a collecting cartridge disposed in the instrument.

23. A method as recited in claim 18, wherein said collecting step comprises collecting the needle in a barrel of the instrument.

24. A method as recited in claim 17, wherein said suturing step comprises pulling the needle out of the needle holder with a needle catcher.

25. A method as recited in claim 24, wherein said suturing step further comprises moving the needle holder and the needle catcher through arcuate grooves formed in the barrel.

26. A method as recited in claim 17 wherein said dispensing step comprises dispensing the needle from a dispensing cartridge disposed in the instrument.

27. A method as recited in claim 17, wherein said dispensing step comprises dispensing a needle from a barrel of the instrument.

28. A method of loading and unloading needles in a suturing instrument comprising:
   loading needles into a needle dispensing cartridge;
   inserting the needle dispensing cartridge into the suturing instrument;
   transferring the needles to a needle collecting cartridge disposed in the instrument; and removing the collecting cartridge from the instrument.

29. A method as recited in claim 28, wherein said inserting step comprises inserting the needle dispensing cartridge in a barrel of the suturing instrument.

30. A method as recited in claim 28, wherein said removing step comprises removing the needle collecting cartridge from the barrel of the instrument.

31. A multiple needle suturing instrument for suturing with a plurality of needles, comprising:
- an elongated barrel having a proximal end and an opposite distal end and defining a longitudinal opening extending between the proximal and distal ends, the opening containing the plurality of needles;
- at least one needle holder;
- a needle dispensing mechanism operative to dispense the plurality of needles from the opening, one at a time, to the at least one needle holder; and
- a needle collecting mechanism operative to collect needles from the at least one needle holder, the collected needles being retained within the opening.

32. A multiple needle suturing instrument according to claim 31, wherein the at least one needle holder is disposed adjacent the distal end and moves into the opening to grasp one of the plurality of needles and outwardly from the opening for suturing with the grasped needle.

33. A multiple needle suturing instrument according to claim 31, further comprising another needle holder.

34. A multiple needle suturing instrument for suturing with a plurality of needles, comprising:
- at least one needle holder;
- a needle dispensing mechanism operative to dispense the plurality of needles, one at a time, to the at least one needle holder; and
- a needle collecting mechanism operative to collect needles from the at least one needle holder being disposed between the needle dispensing mechanism and the needle collecting mechanism.

* * * * *